United States Patent [19]

Karapita

[11] Patent Number: 4,673,154
[45] Date of Patent: Jun. 16, 1987

[54] SUSPENSION DEVICE

[76] Inventor: Alexander D. Karapita, 38 Robinter Drive, Willowdale, Ontario, Canada, M2M 3R2

[21] Appl. No.: 510,643

[22] Filed: Jul. 5, 1983

[51] Int. Cl.⁴ .............................................. A47H 1/10
[52] U.S. Cl. ..................................... 248/320; 269/69; 248/327
[58] Field of Search ............... 248/320, 327, 343, 323, 248/324, 289.1, 291, 293; 403/162, 161, 158, 148, 113, 117; 269/69, 74; 384/428, 441

[56] References Cited

U.S. PATENT DOCUMENTS

| | | | |
|---|---|---|---|
| 2,919,942 | 1/1960 | Bechtel | 384/428 |
| 2,954,251 | 9/1960 | Reuter et al. | 403/162 |
| 3,220,756 | 11/1965 | Templeton | 403/162 |
| 3,774,873 | 11/1973 | Krogsrud | 248/324 |
| 3,945,597 | 3/1976 | Klein | 248/327 |
| 4,166,602 | 9/1979 | Nilsen et al. | 248/324 |
| 4,268,096 | 5/1981 | Cain et al. | 384/428 |

*Primary Examiner*—Ramon O. Ramirez
*Attorney, Agent, or Firm*—Sim & McBurney

[57] ABSTRACT

A device from which articles can be suspended comprising a suspension post, a first rotor, a first bearing having a shaft and a race rotatable about the shaft, the first end of said shaft of said first bearing being rigidly mounted with respect to said suspension post, said rotor being carried by said race of said first bearing for rotation about the axis of the shaft of said first bearing, a first bearing coupler rigidly mounted with respect to said shaft of said first bearing and adapted to receive in rigid coupling relation one end of the shaft of a second bearing that is similar to said first bearing, an article support arm assembly carried by said rotor.

11 Claims, 3 Drawing Figures

SUSPENSION DEVICE

This invention relates to a device for suspending articles such as pieces of hospital equipment.

In hospital practice there is a requirement for a device that is capable of suspending pieces of apparatus and equipment so that the apparatus or piece of equipment can be manipulated to different positions in use. For example, it may be required to have a piece of apparatus for testing blood pressure readily available for use with a patient, but easily maneuvered into a position where it is not in the way of other treatment when not in use. There is also a requirement for suspending intravenous feeding equipment that varies depending upon circumstances and requires that the equipment be moveable with respect to the patient. The number of devices to be suspended varies from one situation to another.

Adjustable suspension apparatus for these purposes is available, but it is cumbersome and relatively inconvenient to use. The available equipment consists of a series of horizontally disposed arms pivotally connected at their ends by vertically extending pins so that they can be disposed at various angles towards each other to permit the projection of the end of the free arm to a desired location. The arrangement is flimsy and the mechanicl design is difficult from a strength point of view at the vertically extending pins. The use of more than one arm in a particular application is particularly cumbersome.

It is the purpose of this invention to provide a device from which this equipment can be suspended that is easier to manipulate and avoids the cumbersome nature of the prior devices, especially in those cases where there is a requirement to suspend apparatus from more than one support arm.

A device from which articles can be suspended according to this invention comprises a suspension post, a first rotor, a "first bearing having a shaft with two ends and a race rotatable about the shaft, one end of the shaft of said first bearing being rigidly mounted with respect to said suspension post, said rotor being carried by said race of said first bearing for rotation about the axis of the shaft of said first bearing, a first bearing coupler rigidly mounted with respect to said shaft of said first bearing and adapted to receive in rigid coupling relation one end of the shaft of a second bearing that is similar to said first bearing, an article support arm assembly carried by said rotor. The invention will be readily understood after reference to the following detailed specification read in conjuntion with the drawings.

In the drawings:

FIG. 3 is a perspective illustration of a mounting sleeve and a rotor control base.

Figure 1:
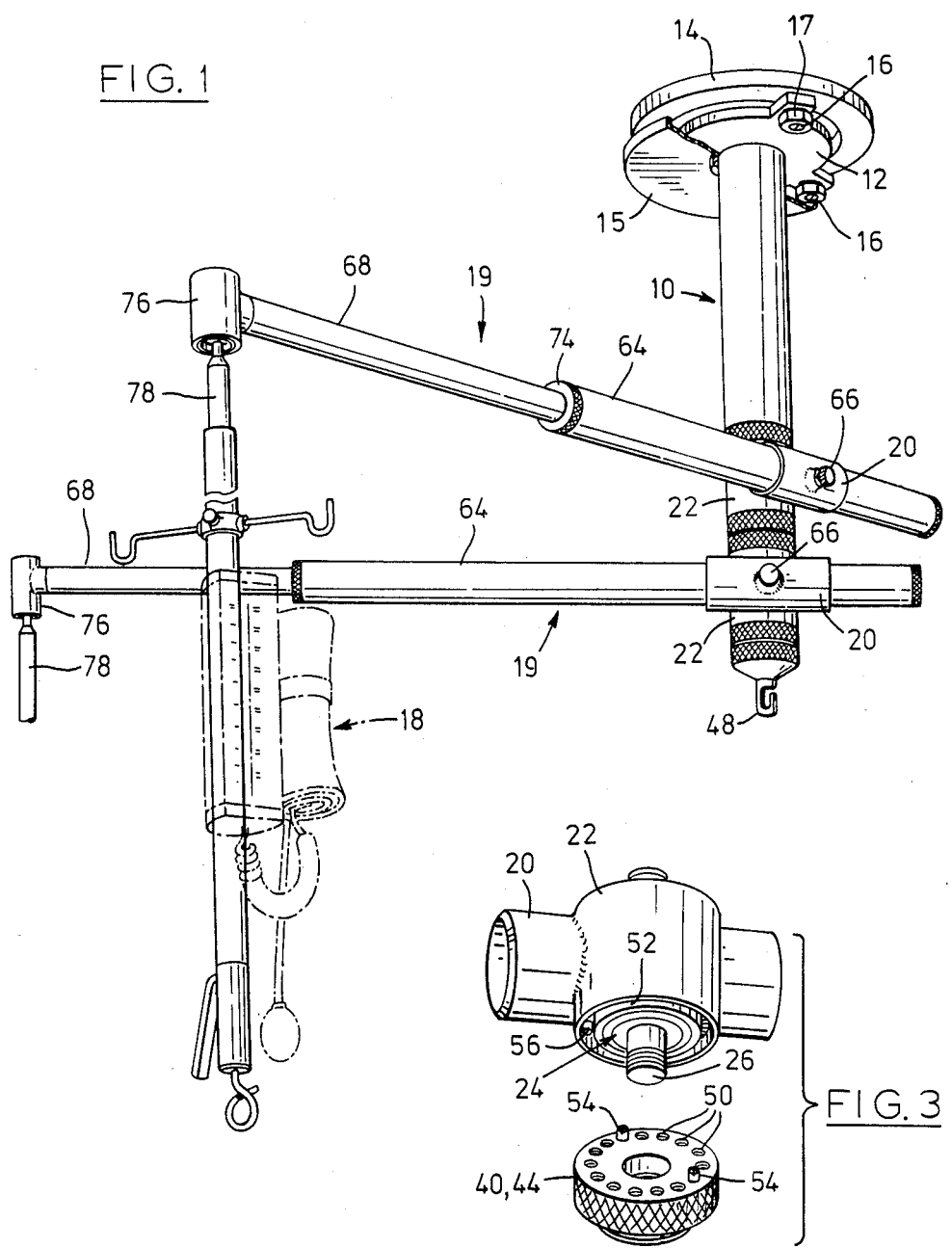
FIG. 1 is a perspective illustration of a device according to the invention.

The instrument support device illustrated in the drawings comprises a suspension post 10 that extends downwardly from a mounting plate 12 which, in turn, is suspended from a mounting ring 14 by means of bolts 16. The mounting ring 14 is firmly secured to a ceiling and the post 10 can be adjusted for verticality by rotating the sleeves 17 which thread into the mounting plates 12 and rotate freely about the bolts 16. In this manner the mounting plate is carried upwardly or downwardly of the stationary bolt 16 at the location of the bolt to achieve verticality of the post. A trim plate 15 may be employed to cover the mounting plate 12 and ring 14.

The unit illustrated has two instrument support arm assemblies generally indicated by the numeral 19 and apparatus 18 for measuring blood pressure has been illustrated as suspended from one of the support arm assemblies.

Each of the support arm assemblies is retained within a mounting sleeve 20 the axis of which is offset with respect to the axis of a rotor 22. The rotors 22 are each in turn fixed to the outer bearing race of a bearing unit generally indicated by the numeral 24 that comprises a shaft 26 and an outer bearing race 28 rotatable with respect to the shaft and capable of withstanding loads between the outer bearing race and the shaft in a direction axially of the shaft. The bearing assembly (not illustrated) permits relative rotation between the race and the shaft. Bearing units of this general specification are readily available on the market and a unit which has been used with success in the emodiment of the invention illustrated is one manufactured by Fag Bearings Limited and identified as their No. WK 2662.

Figure 2:
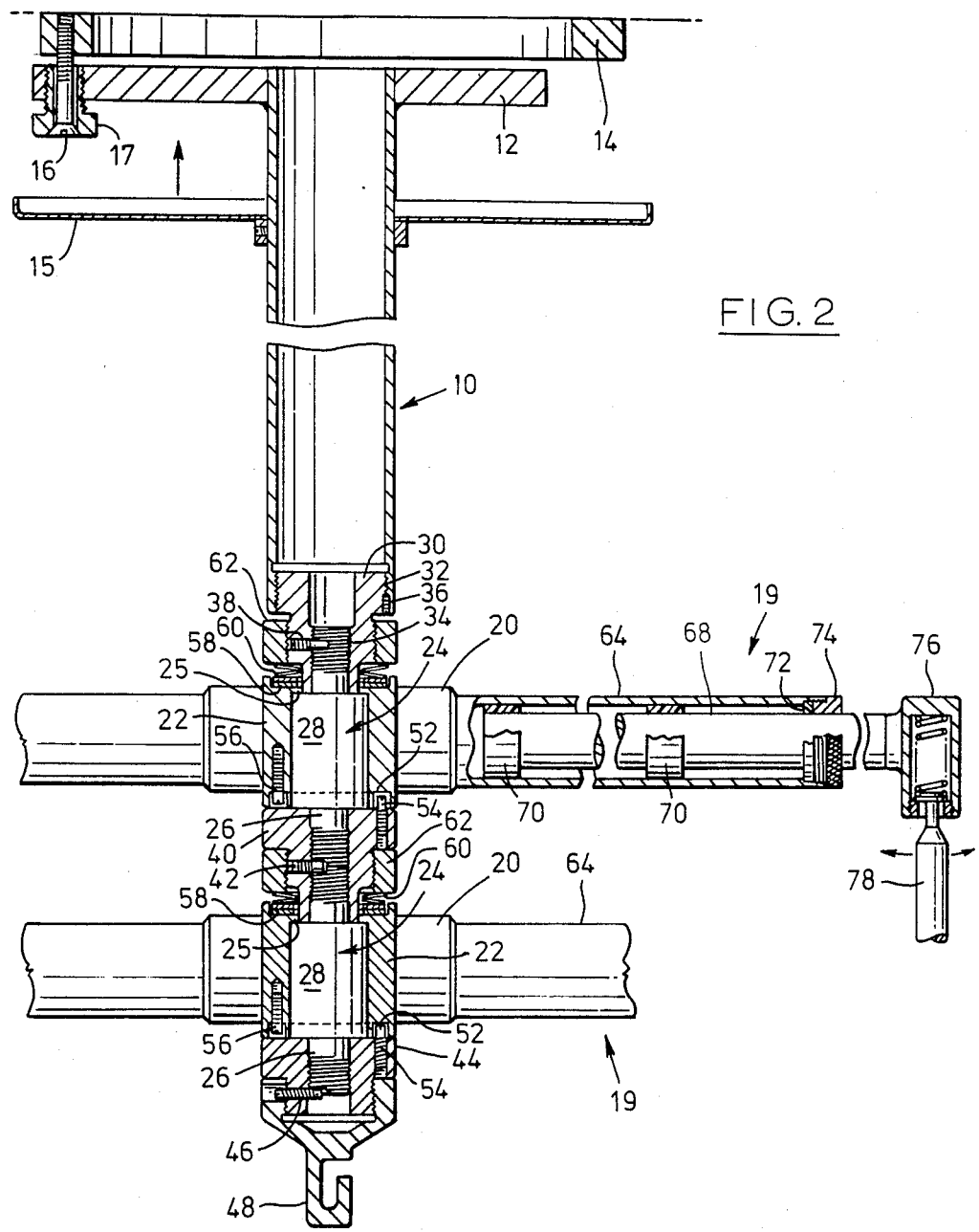
FIG. 2 is a side illustration of the device partly in cross-section.

The rotors 22 from which the supports arms 19 extend are press fitted over the outer races 28 of their respective bearing units and rotate therewith in use. It will be noted from FIG. 2 that there is a flange 25 on the inside top of the central opening in the rotors that sits on the outer marginal edge of the race of the bearing unit.

The shafts 26 of the bearing units do not rotate. They are maintained rigid with respect to the suspension post 10. In this respect a coupler fitting 30 is threaded into the bottom end of the post as at 32 and the threaded end of the shaft of the upper bearing assembly is threaded into the coupler fitting as at 34. A threaded pin 36 keeps the coupler fitting from rotation with respect to the post and a pin 38 keeps the shaft of the upper bearing unit from rotating with respect to the coupler fitting 30. Thus, the shaft 26 of the upper bearing assembly is fixed from rotation with respect to the suspension post 10 and the bearing assembly will permit free rotation of the rotor which is press fitted onto the race of the bearing unit with respect to the shaft of the bearing unit.

The shaft of the lower bearing unit is threaded into the coupler 40 which, in turn, is threaded onto the lower end of the shaft 26 of the upper bearing unit. A pin 42 extends through the body of the coupler for the upper rotor and the shafts of the two bearing assemblies to prevent relative rotation between the connected parts. Thus, the shaft of the lower bearing assembly is fixed with respect to the shaft of the upper bearing assembly and with respect to the suspension post 10.

The lower rotor 22 and its bearing assembly also have a coupler 44 that threads onto the lower end of the shaft 26 of the lower bearing assembly with which it is rigidified against rotation by a pin 46 that passes through the coupler and through the bearing shaft. The rotor control bases will be referred to in detail shortly.

In this respect the brake collar 62, to be referred to later, has a radially extending bore (not shown) through which pin 42 can be mounted and demounted.

A hook assembly 48 is threaded onto the coupler of the lower bearing assembly. However, it will be appreciated that it would also have been possible to suspend a further bearing assembly and rotor in the same manner that the lower bearing assembly is secured to the upper bearing assembly in the embodiment of the invention illustrated. The significant thing about the unit is its ability for expansion by merely adding bearing assemblies and their related rotors in line.

Reference will now be made to the couplers 40 and 44. They are the same in operation and, in addition to providing for modular expansion, function to limit the amount of rotation of the rotors about their respective shafts. In hospital or like use the support arm assemblies 19 usually must be rotated in a limited arc only. Further rotation is not desired and could be dangerous. It will be recalled that the couplers 40 and 44 are not rotatable with respect to the suspension post 10. As shown in FIG. 3, a continuous series of threaded through holes 50 extend around the edge of each rotor base and threaded pins 54 are inserted into two of each series of spaced apart holes. The spacing of the pins defines the arc of rotation of the couplers and the instrument support arm assembly that is carried thereby.

Each of the rotors 22 have an annular channel 52 into which the free ends of the pins 54 extend. The annular channel has a stop pin 56 that extends thereacross. Stop pin 56 on the rotor is located between the free ends of the two stop pins 54 on the coupler so that the engagement of the rotor stop pin with one of the pins 54 limits rotation of the rotor in one direction and the engagement of the rotor stop pin with the other of the pins 54 limits rotation of the rotor in the other direction. It will be apparent that by appropriate spacing of the pins 54 in the holes 50 that the degree of rotation of the rotors about the shafts of the bearing units and, therefore, the suspension post 10 can be adjusted.

It is desirable that the freedom of rotation of the rotors should be subject to braking. The bearing between the shaft of the bearing units and the drums of the bearing units is a free running bearing and would, of itself, likely be too free for hospital use. Braking is achieved by means of a brake device which comprises friction brake washers 58 spring washers 60 and a brake tensioning ring 62. Brake tensioning ring 62 is threaded onto the suspension fitting 30 and can be turned to cause it to travel upwardly or downwardly with respect to the fitting whereby to release or increase the compression of the brake tensioning washers 60. Increase of compression on the washers increases the braking force of the friction brake washers 58 on the rotor to dampen rotation of the rotor with respect to its bearing and the suspension post 10.

The spring washers must be locked against rotation for proper braking action and in this respect they each have a radially inwardly projecting leg (not shown) that engages in a detent in the coupler to prevent rotation in use.

The braking arrangement in respect of the lower rotor is the same as the upper rotor. The arrangement has been described in respect of the numbers applied to the parts for the upper rotor.

The instrument support arm assembly 19 comprises a tubular member 64 which is clamped by means of a thumb adjusting screw 66 (FIG. 1) within the sleeve 20 of the rotor 22 and a tubular member 68 that telescopes with respect thereto.

Nylon bearings 70 are mounted within the tubular member 64 to provide a good bearing for the slideable member 68. Bearings 70 are mounted on the slideable member. A bearing 72 is secured in place at the end of the tubular member 64 by means of a threaded sleeve 74. Outward extension of the member 68 is limited by the contact of one of the bearing members 70 with the bearing 72.

The article to be suspended such as the blood pressure testing item 18 is suspended from the fitting 76 at the free end of tubular member 68. It comprises a rod 78 that is swingably mounted in the fitting 76.

The position of the instrument support arm assembly 19 within the sleeve is adjustable longitudinally of the sleeve by releasing the set screw 66, adjusting the assembly and retightening the set screw. Counterbalancing of the arm about the rotor is possible in cases where required.

The assembly and adjustment of the unit from the drawings will be apparent to a person skilled in the art. The suspension fitting 48 at the bottom of the unit is merely threaded out of position after release of the pin 46. Removal of the fitting 48 permits access to the pins 54. They can be relocated as indicated above in the series of holes 50 as shown in FIG. 3 to control the arc of swing of the rotor and its instrument support arm assembly. Access to the pins that adjust the upper rotor and its support art assembly is gained by losing the appropriate locking pins to remove the lower coupler 44, the lower rotor 22 and brake ring 62.

In use, the unit permits the suspension of multiple instrument support arm assemblies in a limited amount of space and provides an instrument suspension means that is efficient and easy to use. The telescoping arms are easy to adjust longitudinally of themselves and can be easily located in any desired direction within the arc of adjustment. Moreover, the arc of rotation can be limited to suit the purposes of any particular requirement. Tensioning of the rotation of the rotors is simply achieved with the adjustment ring. In summary, the unit represents a very much simplified means of adjustment for suspending articles required to service a sick person and provides multiple suspension means as required in a minimum of space.

I claim:

1. A device from which articles can be suspended comprising:
   a suspension post;
   a first rotor;
   a first bearing having a shaft with two ends and a race rotatable about the shaft;
   one end of said shaft of said first bearing being rigidly mounted with respect to said suspension post;
   said rotor being carried by said race of said first bearing for rotation about the axis of the shaft of said first bearing;
   a first bearing coupler rigidly mounted with respect to said shaft of said first bearing and adapted to receive in rigid coupling relation one end of the shaft of a second bearing that is similar to said first bearing;
   an article support arm assembly carried by said rotor.

2. A device from which articles can be suspended as claimed in claim 1 having braking means for adjustably braking the rotation of said rotor with respect to said shaft of said first bearing.

3. A device from which articles can be suspended as claimed in claim 1 having stop means rigid with respect to said shaft of said bearing and cooperating stop means rigid with respect to said rotor for limiting the arc of rotation of said rotors about said shaft of said first bearing.

4. A device from which articles can be suspended as claimed in claim 2 having stop means rigid with respect to said shaft of said bearing and cooperating stop means rigid with respect to said rotor for limiting the arc of rotation of said rotors about said shaft of said first bearing.

5. A device from which articles can be suspended as claimed in claim 1 wherein said stop means that are rigid with respect to said shaft are carried by said coupler.

6. A device from which articles can be suspended as claimed in claim 2 wherein said stop means that are rigid with respect to said shaft are carried by said coupler.

7. A device from which articles can be suspended as claimed in claim 1 in which said coupler comprises a collar that extends around the shaft of said bearing assembly.

8. A device from which articles can be suspended as claimed in claim 2 in which said coupler comprises a collar that extends around the shaft of said bearing assembly.

9. A device from which articles can be suspended as claimed in claim 2 in which said braking means comprises a braking collar threadedly mounted for rotation with respect to said shaft of said first bearing for movement longitudinally of said shaft of said first bearing, a brake shoe and brake spring assembly operative between said braking collar and said rotor.

10. A device from which articles can be suspended as claimed in claim 2 in which said braking means comprises a braking collar threadedly mounted for rotation with respect to said shaft of said first bearing for movement longitudinally of said shaft of said first bearing, a brake shoe and brake spring assembly operative between said braking collar and said rotor, stop means rigid with respect to said shaft of said bearing and cooperating stop means rigid with respect to said rotor for limiting the arc of rotation of said rotors about said shaft of said first bearing.

11. A device from which articles can be suspended as claimed in claim 1 having a second bearing rigidly coupled to said first bearing coupler, a second rotor similar to said first rotor carried by the race of said second bearing for rotation about the axis of the shaft of said second bearing assembly, a second bearing coupler rigidly mounted with respect to the shaft of said second bearing and adapted to receive in rigid coupling relation one end of a third bearing that is similar to said first bearing and said second bearing.

* * * * *